United States Patent [19]

Zebehazy

[11] Plant 4,111

[45] Sept. 27, 1977

[54] *PIERIS JAPONICA* - ZEBRIS VARIETY

[75] Inventor: Alex J. Zebehazy, Perry, Ohio

[73] Assignee: The Conard-Pyle Company, West Grove, Pa.

[21] Appl. No.: 688,365

[22] Filed: May 20, 1976

[51] Int. Cl.[2] ..... A01H 5/00

[52] U.S. Cl. ..... Plt./54

[58] Field of Search ..... Plt./54

*Primary Examiner*—Robert E. Bagwill

*Attorney, Agent, or Firm*—Burns, Doane, Swecker & Mathis

[57] ABSTRACT

The invention relates to a new and distinct variety of *Pieris japonica* of the evergreen shrub type wherein the new shoots exhibit a bright and distinctive reddish-purple color on the new leaves and stems in combination with a vigorous decorative upright growth habit, abundant mature leaves of larger size having a darker green color which is maintained over the winter, flowers which open and mature seven to ten days later, and young stems and branches which exhibit a more even reddish winter color.

2 Drawing Figures

SUMMARY OF THE INVENTION

My invention relates to a new and distinct variety of Pieris which was discovered by me among plants of the unpatented variety known as *Pieris japonica.* Said discovery having been made by me in May, 1962.

For many years prior to 1962, I had been collecting open pollinated seed from *Pieris japonica* plants that showed more reddish color in the new foliage than others. With each generation, I selected seed from plants in this manner, with each generation showing slightly more distinctive and pronounced reddish color.

This particular plant was selected from a group of open pollinated seedlings growing in a field row in my nursery. I was first attracted to this plant because of the distinctive, bright, reddish color of the newly formed leaves. It was growing among other open pollinated seedlings of *Pieris japonica* of similar color and growth, but the color of this particular plant stood out as being more red and distinctive than any of those growing around it.

The primary object of my selection work was to produce a new *Pieris japonica* of bright and distinctive coloration of uniform habit of growth yet vigorous, freely branched and compact form. This objective was realized along with other desirable improvements, as evidenced by the following unique combination of characteristics which are outstanding in my new variety and which distinguishes it from all other Pieris of which I am aware.

My discovery differs from other *Pieris japonica* by:

1. The new shoots come out with distinctive, brilliant reddish-purple color on the newly formed leaves and on the new stem bearing these leaves. All new shoots through the growing season have the same brilliant reddish color.

2. As the leaves reach maturity, they have a distinctive darker green color.

3. An even habit of growth, upright, freely branched and compact yet vigorous.

4. Winter color of a darker green with less leaf spotting and discoloration than is customary on other *Pieris japonica.*

5. Flowering 7 to 10 days later than other *Pieris japonica.*

6. Tendency to produce a higher percentage of plants of uniform habit and growth than other *Pieris japonica.*

7. Studies show that my discovery is more resistant to Phytopthora species, which causes dieback and leaf spotting, than other *Pieris japonica.*

8. Mature foliage and growth habit are distinct from other *Pieris japonica*—the plants are more freely branched, leaves are larger in size and occur more abundantly giving my new discovery a more dense and full appearance than other *Pieris japonica* grown under the same conditions.

The typical mature leaves of the present variety measure approximately 3 to 3¼ inches in length and approximately ⅝ to ¾ inch in width. The typical mature leaves of the regular *Pieris japonica* measure approximately 2⅛ to 2½ inches in length and approximately ½ to ¾ inch in width.

9. Stems and young branches have a reddish coloration in winter more pronounced, darker and more widely distributed over stems and branches than other forms of *Pieris japonica.*

10. My Pieris is well suited to the needs and demands of the environment for ornamental plants, having decorative year-round value and tolerating a wider range of climatic conditions and adaptable to a more wide range of decorative uses.

11. Unprotected plants of my new invention have survived temperatures below 0° F. where other plants of *Pieris japonica* have suffered injury and burn to the terminal foliage, while my new discovery was free from all injury and burn.

Observations of my new discovery have been made on my nursery near Perry, Lake County, Ohio, where I have been involved with growing and selling plants all of my working life, and with operating my own nursery with the specialty of propagating and growing *Pieris japonica.* The detailed descriptions and comparisons are made from plants of my discovery propagated by me and grown on my nursery along with plants of other *Pieris japonica,* propagated and grown by me under similar growing conditions on my nursery.

Asexual reproduction of my new discovery by cuttings have been performed by me at my nursery at Perry, Ohio, since 1962. This propagation shows that the unique combination of characteristics and distinctive color come true to form and are established and transmitted through succeeding propagations.

DETAILED DESCRIPTION OF THE DISCLOSURE

Figure 1:
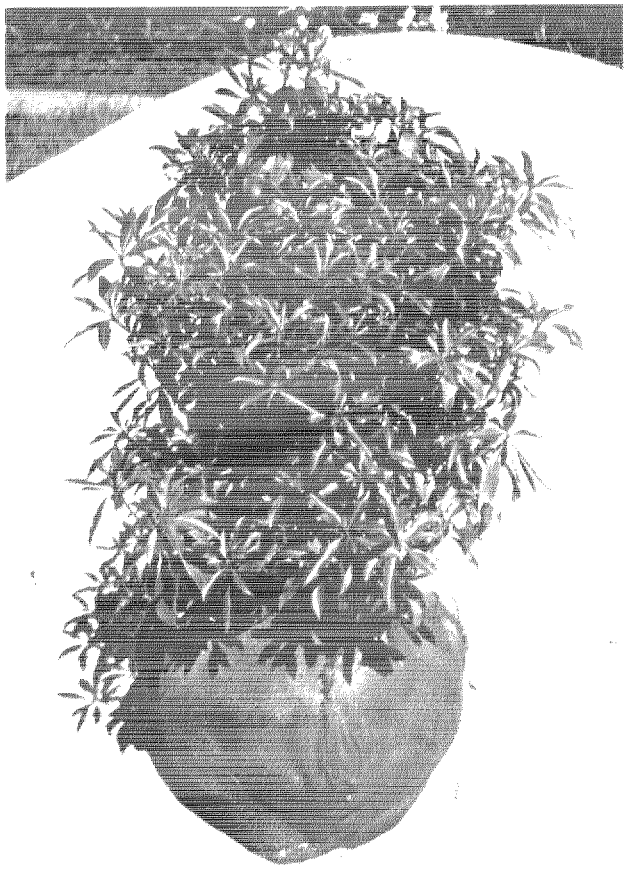
FIG. 1 shows a typical plant of the new variety as depicted in color as nearly true as possible in a color illustration of this nature.
Figure 2:
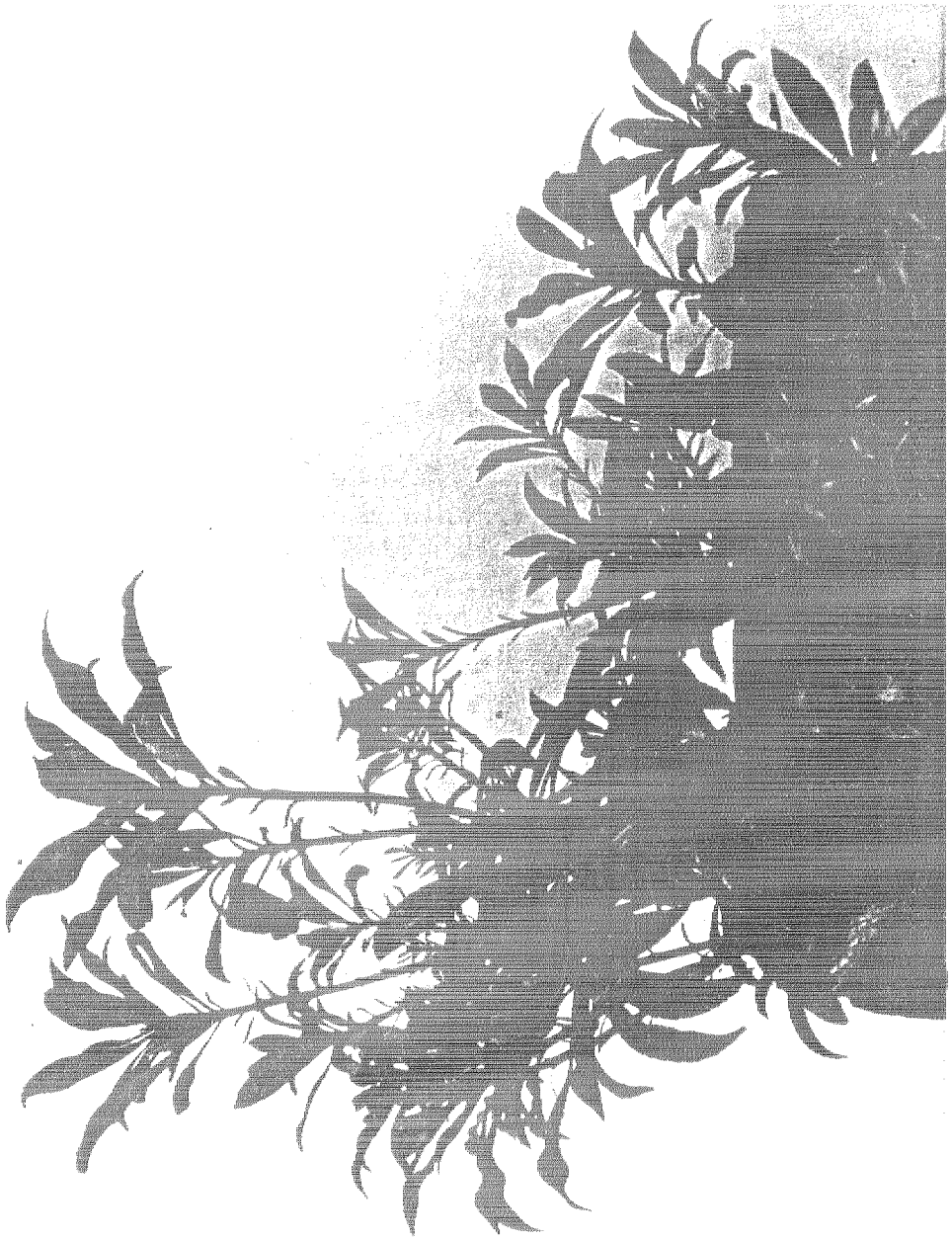
FIG. 2 shows typical specimens of the vegetative growth of my new discovry in different stages of development as depicted in color as nearly true as possible in a color illustration of this nature.

The following description was made May 12, 1975, from plants growing in full sun in West Grove, Pa. Color designations are the Royal Horticultural Society Colour Chart.

FOLIAGE

Juvenile foliage before the leaf shape is apparent is 144B at the tips, becoming 145B at the point of attachment. Stems are 144B.

Juvenile foliage: When fully unfolded and the leaf shape is apparent:

*Upper side.*—A blend of shades 150B and 146B, penciled 175A around the edge of each leaf from the point of attachment to two-thirds of the way up the leaf.

*Under side.*—A blend of 144C and 146A, penciled with 175A from two-thirds to three-quarters of the way up the leaf from the point of attachment. At the point of attachment the stem is 175A with stems blending 175A, 178B and 178C.

As young foliage begins to mature:

*Upper side.*—183A blending to between 183A and 45A near point of attachment. Stem at point of attachment is 183B.

*Under side.*—177B with veins of 183A. The small point at the tip of the leaf is 151C on both the upper and lower side of the leaf. Stem color is a blend of 178A and 182B. Small juvenile foliage on the side of the stem is 160B with 178B predominant at the tip on the under side of the juvenile foliage.

Semi-mature foliage:

*Upper side.*—178B gradually becoming between 153A and 151A near the point of attachment. Stems at the point of attachment are 178A. Leaf veins 178B.

*Under side (as observed with the leaf resting on white bond paper).*—Gives the appearance of 153B with a definite cast as in 182B. Leaves can be a much deeper shading of 182B on both upper and under side of the leaf. Veins are 184A. A tip of 145A is apparent on both the upper and under side of the leaf.

*Stems (at point of attachment).*—176A.

*Stems.*—166B.

Mature foliage (year old growth inside the plant):

*Upper side.*—146A. Center vein of the leaf is 154C, becoming 154C with lines of 166B down the side of the stem near the point of attachment.

*Under side.*—162A, becoming 154C with lines of 166B down the side of the stem near the point of attachment.

*Branches.*—166A.

Mature branches (near the base of the plants): 199B.

Having thus described and illustrated my new variety of *Pieris japonica* what is claimed as new and desired to be secured by Letters Patent is:

1. A new and distinct variety of *Pieris japonica* of the evergreen shrub type substantially as shown and described, characterized particularly as to novelty by the unique combination of the new shoots having brilliant reddish-purple color on the new leaves and stems; the highly decorative growth of even, compact, upright habit, vigorous and freely branched; greater winter hardiness and disease resistance; with more abundant leaves of larger size with darker green color and which hold this color over the winter; with flowers which open and mature 7 to 10 days later, and young stems and branches having a more even reddish winter color.

* * * * *